United States Patent [19]

Bedeschi et al.

[11] Patent Number: 5,457,193

[45] Date of Patent: Oct. 10, 1995

[54] HYDROXY PROTECTING GROUP REMOVAL IN PENEMS

[75] Inventors: Angelo Bedeschi, Milan; Franco Zarini, Settimo Milanese, both of Italy

[73] Assignee: Farmitalia Carlo Erba S.r.l., Milan, Italy

[21] Appl. No.: 400,013

[22] Filed: Mar. 6, 1995

Related U.S. Application Data

[63] Continuation of Ser. No. 51,616, Apr. 23, 1993, abandoned.

[30] Foreign Application Priority Data

May 14, 1992 [GB] United Kingdom .................. 9210371

[51] Int. Cl.⁶ .................................................. C07D 499/00
[52] U.S. Cl. ........................................ 540/310; 540/312
[58] Field of Search ................................. 540/310, 312

[56] References Cited

FOREIGN PATENT DOCUMENTS 0295100  12/1988  European Pat. Off. .

OTHER PUBLICATIONS

Tetrahedron Letters, No. 41, 1979, pp. 3981–3982, R. F. Newton, et al., "Excellent Reagent For The Removal Of The T–Butyldimethylsilyl Protecting Group".
Chemical Abstracts, vol. 112, No. 21, 1990, Abstract No. 197969h, JP-A-1 254 656, Oct. 11, 1989.

*Primary Examiner*—Nicholas Rizzo
*Attorney, Agent, or Firm*—Oblon, Spivak, McClelland, Maier, & Neustadt

[57] ABSTRACT

The present invention relates the removal of t-butyldimethylsilyl protecting groups in the preparation of penems which are useful antibiotics. The invention provides a process for preparing a compound of the formula I:

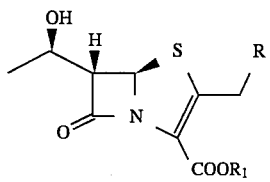

wherein R is a free or protected hydroxy or amino group or an alkoxy, acyloxy or an optionally substituted carbamoyloxy group, and $R_1$ is selected from:

a) hydrogen;
b) a $C_2$–$C_4$ alkenyl group;
c) a p-$NO_2$ benzyl group;
d) a linear or branched alkanoyloxy $C_1$–$C_2$ alkyl group; and
e) (2-oxo-1,3-dioxolen-4-yl)methyl optionally substituted by $C_1$–$C_4$ alkyl at the 5-position or a pharmaceutically acceptable salt thereof, which process comprises reacting a compound of the formula II:

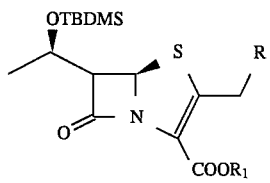

9 Claims, No Drawings

HYDROXY PROTECTING GROUP REMOVAL IN PENEMS

This application is a continuation of application Ser. No. 08/051,616, filed on Apr. 23, 1993, now abandoned.

The present invention relates to a new method for the removal of the t-butyldimethylsilyl (TBDMS) protecting group for preparing penems. It is known that the TBDMS protecting group is widely used in the β-lactam field especially as protective group of the hydroxyethyl side-chain in the synthesis of useful penem and carbapenem antibiotics, see our U.S. Pat. Nos. 4,631,150 and 4,952,577.

Usually the removal of the TBDMS group from the hydroxyethyl side-chain is performed by the use of tetrabutyl ammonium fluoride (TBAF), but difficulties may arise from the use of this deprotecting agent. Moreover the high cost of TBAF makes it not suitable for industrial scale production.

Other known literature methods are unsuitable for penems, owing to the limited stability of the molecule in both acidic and basic conditions.

The present invention describes a new process for the removal of TBDMS group from the hydroxyethyl side chain of penems which provides soft conditions which are necessary for the sensitive penems and gives high yield (up to 90%) with small amounts of degradation by-products.

The present invention comprises reacting a compound of the formula II

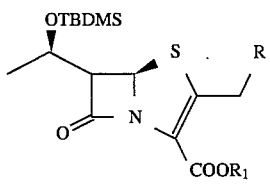

wherein R is a free or protected hydroxy or amino group or an alkoxy, acyloxy or an optionally substituted carbamoyloxy group, and $R_1$ is selected from:

a) hydrogen;

b) a $C_2$–$C_4$ alkenyl group;

c) a p-$NO_2$ benzyl group;

d) a linear or branched alkanoyloxy $C_1$–$C_2$ alkyl group; and e) (2-oxo-1,3-dioxolen-4-yl)methyl optionally substituted by $C_1$–$C_4$ alkyl at the 5-position, with an aqueous solution of a hydrogen halide to give a compound of formula I:

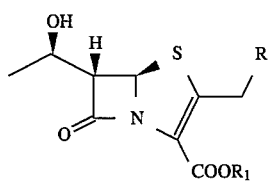

wherein R and $R_1$ are as defined above, and, if desired, converting a compound of formula I into a pharmaceutically acceptable salt.

The reaction is typically carried out in an organic solvent. The hydrogen halide solution suitably has a concentration of from 0.01M to 0.5M. Typically the reaction is carried out at a temperature of from −20° C. to 60° C., preferably from 0° C. to 40° C. A typical time for the reaction is from 1 hour to 3 days, preferably from 4 hours to 1 day. In a preferred embodiment the reaction is carried out in an organic solvent, the aqueous solution of hydrogen halide having a concentration of from 0.01M to 0.5M, at a temperature of from −20° C. to 60° C., preferably from 0° C. to 40° C., for a time of from 1 hour to 3 days, preferably from 4 hours to 1 day.

Preferably, the molar ratio hydrogen halide: compound of formula II is from 1:1 to 6:1, more preferably 1:1 to 3:1. In a further preferred embodiment, the reaction is carried out in an organic solvent, the aqueous hydrogen halide solution has a concentration of from 0.01M to 0.5M, the temperature is from −20° C. to 60° C., the reaction time is from 1 hour to 3 days and the molar ratio hydrogen halide: compound of formula II is from 1:1 to 6:1.

The preferred groups which R may represent include a free or protected hydroxy or amino group, a $C_1$–$C_4$ alkoxy group, and preferably a methoxy group; $C_1$–$C_5$ alkanoyloxy group, and preferably an acetoxy group; an optionally substituted $C_1$–$C_4$ carbamoyloxy group, and preferably an unsubstituted carbamoyloxy group. An optional substituent of the $C_1$–$C_4$ carbamoyloxy group is for example, a $C_1$–$C_4$ alkyl group. A suitable hydroxy protecting group is, for example, a p-$NO_2$ benzyloxycarbonyl, allyloxycarbonyl or tetrahydropyranyl group. A suitable amino protecting group is, for example, a $C_1$–$C_4$ alkanoyl, benzoyloxycarbonyl or t-butoxycarbonyl group. Preferably $R_1$ is a group known to be chemically hydrolyzable on a penem nucleus, such as a p-$NO_2$ benzyl or a $C_2$–$C_4$ alkenyl group, for example, a propenyl group, preferably an allyl group, or a group which is known to be hydrolyzable in vivo, such as a straight or branched alkanoyloxy $C_1$–$C_2$ alkyl group, for example, an acetoxyethyl, pivaloyloxymethyl or 1-acetoxyethyl group.

A preferred example of an optionally substituted (2-oxo-1,3-dioxolen-4-yl)methyl group is a (5-methyl-2-oxo-1,3-dioxolen-4-yl) methyl group.

Suitable organic solvents, include polar solvents, such as dimethylacetamide, dimethylformamide (DMF), acetonitrile, tetrahydrofuran (THF) and dioxane. Preferred solvents include DMF, acetonitrile and THF.

Suitable hydrogen halides include HF, HCl, HBr and HI, preferably HF, HCl and HBr.

The starting compounds of the formula II are known compounds or may be prepared as described in the above cited patents.

Due to the low cost of the reagents and to high yields, and easy and mild reaction conditions this method is particularly useful for the preparation in large scale of a compound of the formula Ia

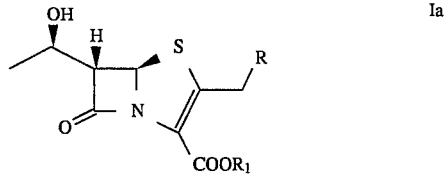

wherein R is a methoxy or carbamoyloxy group and $R_1$ is hydrogen or an acetoxymethyl or 5-methyl-2-oxo-1,3-dioxolen-4-yl methyl group, or a pharmaceutically acceptable salt thereof.

The compounds of the formula I are useful beta-lactam antibiotics or their intermediate when $R_1$ is a chemically hydrolyzable group and may be, if desired, converted into a different compound of the formula I or into a pharmaceutically acceptable salt thereof by performing conventional reactions. The compounds of the formula I may then be formulated together with a pharmaceutically acceptable carrier or diluent. The resulting pharmaceutical compositions may be for oral or parenteral administration.

The following examples illustrate, but not limit the above mentioned process.

EXAMPLE 1

Acetoxymethyl 5(R), 6(S) 6-[1(R)-hydroxyethyl]-2-carbamoyloxymethyl penem-3-carboxylate (FCE 22891)

To a solution of acetoxymethyl (5R, 6S)-6-[1(R)-t-butyl-dimethylsilyloxyethyl- 2-carbamoyloxymethyl-penem-3-carboxylate (0.95 g) in acetonitrile (60 ml) a solution of hydrochloric acid 0.1N (60 ml) in water was added. The reaction mixture was stirred for 24 hrs at room temperature. An aqueous solution of NaHCO$_3$ 8% (about 6 ml) was added. The solution was concentrated to small volume. Ethyl acetate was added, the solution was washed with brine, dried over anhydrous Na$_2$SO$_4$ and evaporated in vacuo. There were obtained 0.6 g of the title compound.
UV (EtOH 95%) $\lambda_{max}$ 327 ($\epsilon$ 7500)
IR (KBr) $\nu_{max}$=3500–3300, 1800, 1760, 1720, 1590 cm$^{-1}$

EXAMPLE 2

Allyl 5(R), 6(S)-6-[1(R)-hydroxyethyl]-2-carbamoyloxymethyl penem-3-carboxylate (FCE 22101 allyl ester)

To a solution of allyl (5R, 6S)-6-[1-(R)-t-butyldimethylsilyloxyethyl]- 2-carbamoyloxymethyl penem-3-carboxylate (0.88 g) in acetonitrile (60 ml) a solution of HCl 0.1N (60 ml) in water was added. The reaction was carried out as in Example 1 to yield 80% (520 mg) of the title compound.
UV $\lambda_{max}$ (CHCl$_3$) 322 nm.
IR $\nu_{max}$ (KBr) 3650–3150, 1775, 1725 and 1700 cm-1.
NMR (CDCl$_3$+DMSO-d$_6$) 1.26 (3H, d, J=6.0 Hz, CH$_3$-CH), 3.86 (1H, dd, J=2 and 7.0 Hz, =CH-CH-CHS), 4.07 (1H, m,CH$_3$-CHOH-CH), 4.64 (2H, m, COOCH$_2$-CH=CH$_2$), 5.07 (1H, s, CH$_3$-CHOH-CH), 5.24 (2H, ABq, J=16 Hz, CH$_2$O-CONH$_2$), 5.20 (1H, d, J=12 Hz), 5.36 (1H, d, J=19 Hz), 5.63 (1H, d, J=2 Hz, CH-CH-S), 5.60–6.10 (1H, m, COOCH$_2$-CH=CH$_2$), 6.06 (2H, CONH$_2$).

EXAMPLE 3

(5-Methyl-2-oxo-1,3-dioxolen-4-yl) methyl 5(R), 6(S)-6- [1(R) hydroxyethyl]-2-methoxymethyl penem-3 -carboxylate ( FCE 25199 )

The reaction was carried out as described in previous examples except (5-methyl-2-oxo-1,3-dioxolen-4-yl)methyl (5R, 6S)-6-[ 1(R)-t-butyldimethylsilyloxyethyl]-2-methoxy penem-3-carboxylate (0.97 g) was used as starting material. The title compound was obtained as a white solid in 70% yield.
UV (CHCl$_3$) $\lambda_{max}$ 326 nm
IR (KBr) $\nu_{max}$ 3450, 1820, 1780, 1725, 1710 cm$^{-1}$.

We claim:

1. A process for preparing a compound of the formula I:

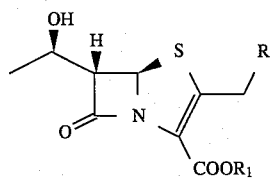

I wherein R is a free or protected hydroxy or amino group or an alkoxy, alkanoyloxy, carbamoyloxy or carbamoyloxy substituted with alky group, and R$_1$ is selected from:
a) hydrogen;
b) a C$_2$–C$_4$ alkenyl group;
c) a p-NO$_2$ benzyl group;
d) a linear or branched alkanoyloxy C$_1$–C$_2$ alkyl group; and
e) (2-oxo-1,3-dioxolen-4-yl)methyl optionally substituted by C$_1$–C$_4$ alkyl at the 5-position, or a pharmaceutically acceptable salt thereof, which process comprises reacting a compound of the formula II:

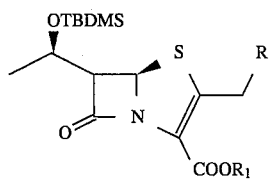

II wherein R and R$_1$ are as defined above and TBDMS represents a t-butyldimethylsilyl group, with an aqueous solution of hydrogen chloride or hydrogen bromide having a concentration of from 0.01M to 0.5M to give a compound of formula I and, if desired, converting a compound of formula I into a pharmaceutically acceptable salt.

2. A process according to claim 1, wherein the reaction is carried out at a temperature of from −20° C. to 60° C. for a time of from 1 hour to 3 days.

3. A process according to claim 1, wherein the molar ratio hydrogen chloride or hydrogen bromide: compound of formula II is from 1:1 to 6:1.

4. A process according to any claim 1, wherein the reaction is carried out in an organic solvent, the aqueous hydrogen chloride or hydrogen bromide solution has a concentration of from 0.01M to 0.5M, the temperature is from −20° C. to 60° C., the reaction time is from 1 hour to 3 days and the molar ratio hydrogen chloride or hydrogen bromide: compound of formula II is from 1:1 to 6:1.

5. A process according to claim 1, wherein R represents a free or protected hydroxy or amino group, a C$_1$–C$_4$ alkoxy group, a C$_1$–C$_5$ alkanoyloxy group a C$_1$–C$_4$ carbamoyloxy group or C$_1$–C$_4$ carbamoyloxy group substituted with alkyl, and R$_1$ represents a p-NO$_2$ benzyl, propenyl, allyl, acetoxymethyl, pivaloyloxymethyl, 1-acetoxyethyl or (5-methyl-2-oxo-1,3-dioxolen-4-yl) methyl group.

6. A process according to claim 1 in which the organic solvent is dimethylacetamide, dimethylformamide, acetonitrile, tetrahydrofuran or dioxane.

7. A process according to any claim 1, wherein the aqueous solution is of HCl.

8. A process according to claim 1 wherein the compound prepared has the formula Ia

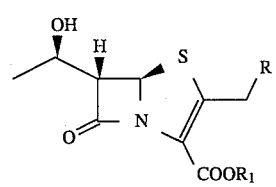

Ia wherein R is a methoxy or carbamoyloxy group and R$_1$ is hydrogen, an acetoxymethyl or (5-methyl-2-oxo-1,3-dioxolen-4-yl) methyl group, or the pharmaceutically acceptable salt thereof.

9. A process according to claim 1 which further comprises admixing the compound of formula (I) or a pharmaceutically acceptable salt thereof, with a pharmaceutically acceptable diluent or carrier.

* * * * *